United States Patent [19]

Ackermann et al.

[11] 4,054,555

[45] Oct. 18, 1977

[54] PROCESS FOR THE PURIFICATION OF HALO-ALDEHYDES

[75] Inventors: Jacob Ackermann, Gorla Minore (Varese); Pierino Radici, Turate (Como), both of Italy

[73] Assignee: Societa' Italiana Resine S.I.R. S.p.A., Milan, Italy

[21] Appl. No.: 685,603

[22] Filed: May 12, 1976

Related U.S. Application Data

[63] Continuation of Ser. No. 321,084, Jan. 4, 1973, abandoned.

[51] Int. Cl.² ....................... C07D 47/14; C07D 47/16

[52] U.S. Cl. ............................ 260/601 H; 260/67 FP

[58] Field of Search .................................... 260/601 H

[56] References Cited

U.S. PATENT DOCUMENTS 2,504,942 4/1950 Williams et al. ................. 260/601 H 2,606,864 8/1952 Cave et al. ....................... 260/601 H

FOREIGN PATENT DOCUMENTS 1,191,355 4/1965 Germany ............................ 260/601

*Primary Examiner*—Donald G. Daus

*Assistant Examiner*—D. B. Springer

*Attorney, Agent, or Firm*—Sughrue, Rothwell, Mion, Zinn and Macpeak

[57] ABSTRACT

Purification of haloaldehydes in a process that consists essentially of a first stage of purification in which the haloaldehydes are brought into contact with an absorbent solid, basic in nature, in the presence of water or free alcohols, and of a second stage of purification in which the halo-aldehydes thus treated are brought into contact with a solid absorbent carrying sulphonic, phosphonic or carboxylic acid groups in the form of salts of alkali or alkaline earth metals.

13 Claims, No Drawings

PROCESS FOR THE PURIFICATION OF HALO-ALDEHYDES

This is a continuation of application Ser. No. 321,084, filed Jan. 4, 1973, now abandoned.

The present invention relates to a process for the purification of halo-aldehydes, more precisely to obtaining those halo-aldehydes in extremely pure form, such as are used in industry in the production of polymers of high molecular weight.

In processes for the production of polymers in which the halo-aldehydes such as for example chloral, are copolymerized with other aldehydes such as for example formaldehyde or related cyclic oligomers, it is essential to use the purest possible monomers. In fact, the presence of impurities in these polymerization mediums has a negative effect on the reactivity of the polymerization system, the consumption of catalyst and also the polymer yield and characteristic features of the polymer itself.

This is probably related to the fact that such impurities can act either as inhibitors on the activity of the catalytic system or as chain transfer agents and can furthermore give rise to secondary reactions with relative undesirable effects.

Therefore, also the polymers obtained may exhibit undesired properties such as colorations or low mechanical strength.

For all these reasons, the polymerizable monomers are subjected to purification by various techniques such as fractional distillation, extractive distillation, adsorption on adsorbent solids and treatment with substances which react to the impurities.

However, the application of the methods described to the purification of halo-aldehydes are not producing completely satisfactory results and the reasons for this failure are probably related to the nature of the halo-aldehydes themselves.

Thus, for example, chloral purification is made difficult by the polar nature of this substance, the closeness of its boiling point with that of water and aqueous hydrochloric acid, and the low chemical stability, particularly vis-a-vis reagents of a basic nature.

Furthermore, in view of the reactivity of this monomer, during the purification treatment, undesired reactioons are readily observed which result in the formation of products of a complex nature, particularly of a polymeric nature.

Since similar difficulties are encountered in the treatment of other halo-aldehydes, the need was felt for a simple and effective method of purification which would make it possible to obtain halo-aldehydes with a high degree of purity, avoiding the disadvantages inherent in prior art purification processes.

The major impurities contained in halo-aldehydes are water and the halo-hydric acid corresponding to the halogen linked to the aldehyde itself. In addition to these, other impurities are normally present, such as organic acids, alcohols, in addition to substances the nature of which is not completely known.

In our earlier patent application Ser. No. 31,632 of Dec. 1, 1970, now abandoned, a process for the purification of polymerizable organic substances was described, which consist essentially in bringing into contact, under particular conditions, the organic substances and an absorbent solid carrying carboxylic, sulphonic or phosphonic acid groups in the form of salts of alkali or alkaline earth metals.

Such absorbents, while making it possible to obtain in extremely pure form the organic polymerizable substances described in the aforesaid patent application, have not been found to be equally effective in the purification of halo-aldehydes, above all because such adsorbents do not make it possible to reduce the halo-hydric acid content to below an acceptable level.

Furthermore, the elimination of halo-hydric acids by treatment of the halo-aldehydes with substances of basic characteristics involves serious problems both due to the low stability of such aldehydes and also because the basic substances constitute catalysts which are active in the polymerization of the aldehydes themselves.

We have now found a process which, while avoiding the disadvantages described, makes it possible virtually completely to eliminate the water, the halo-hydic acids and the other impurities present in the halo-aldehydes.

The process of the present invention is based essentially on the discovery that it is possible to avoid undesired polymerization reactions with respect to the halo-aldehydes, together with other secondary reactions, while the aldehydes are in contact with an absorbent solid of a basic nature, if, in the purification system, a content of water or of free alcohols in excess of a specific level is constantly maintained.

It should be noted that the term water or free alcohols is understood as referring to that fraction of water or alcohol present in the purification system in a form such that it is not absorbed by the absorbent solids.

Therefore, the process of the present invention consists essentially of a first stage of purification in which the haloaldehydes are brought into contact with an adsorbent solid, basic in nature, in the presence of water of free alcohols, and of a second stage of purification in which the halo-aldehydes thus treated are brought into contact with a solid absorbent carrying sulphonic, phosphonic or carboxylic acid groups in the form of salts of alkali or alkaline earth metals.

By means of such a two-fold treatment, carried out under conditions which will be defined hereinafter, it is possible to obtain halo-aldehydes which are completely or virtually bereft of water, halo-hydric acids and other impurities while avoiding undesirable reactions such as the polymerization of the aldehydes themselves and other secondary reactions.

During the course of the present description, halo-aldehydes are understood as being the saturated or unsaturated aliphatic aldehydes which contain at least one atom of fluorine, chlorine or bromine in the molecule.

Examples of such aldehydes are: monochloroacetaldehyde, dichloroacetaldehyde, trichloroacetaldehyde (chloral), monofluoroacetaldehyde, difluoroacetaldehyde, trifluoroacetalehyde, bromoacetaldehyde, and alpha-alpha-beta-trichloro-n-butyraldehyde.

Furthermore, the solid absorbents of a basic nature are those substances which comprise a porous matrix with a specific surface area equal to at least 0.5 sq.m/g and preferably at least 10 sq.m/g, constituted by an organic macroporous, preferably cross-linked substances, or a substance which is in any event insoluble in the monomer which is subjected to purification, the matrix having linked with it hydroxyl groups or primary, secondary or tertiary amine groups or quaternary groups of ammonium, phosphonium or arsonium.

It has been found that the best results are obtained when the macroporous marix has a porous structure with pores having a diameter ranging fromm 20 to $2 \times 10^4$ Angstrom units.

Although any substance of a polymeric nature carrying basic groups and having the characteristics defined hereinbefore may be used for the purpose, in the preferred form of embodiment of the present invention, solid absorbents are used which are polymeric and which consist of ionic or anionic exchange resin.

Ionic and anionic exchange resins are for example those described on page 47 et seq. in "Ion Exchange" by F. Helfferich.

The basic absorbents preferably used in the basic process of the present invention are those which are constituted by anionic exchange resins in which the hydroxyl groups or tertiary amine groups or quaternary ammonic groups are boned to a polystyrene based matrix, or better still a matrix obtained by copolymerizing styrene beads with a divinyl monomer such as divinylbenzene.

Furthermore, absorbent solids bearing salified acid groups are those substances which comprise a porous matrix with a specific surface area equal to at least 1 sq.m/g, constituted by a polymeric, preferably cross-linked, organic substance, or one which is any event insoluble in the monomer which is being purified, the said matrix having linked to it carboxyl, sulphonic or phosphonic groups in the form of salts of alkali or alkaline earth metals.

It has been found that the best results are obtained when the polymeric matrix has a porous structure with pores of a diameter ranging from $10^{1.3}$ to $10^6$ Angstrom units.

Although any substance of a polymeric nature bearing the salified acid groups and having the characteristics defined hereinabove may be used for the purpose, macroporous cationic and anionic exchange resins which have been previously treated in order to convert the acid groups to the form of salts of alkali or alkaline earth metals, are used in the preferred form of embodiment of the present invention.

Cationic ionic exchange resins are for example both described on page 29 et sequ. of "Ion Exchange" by F. Helfferich.

Of the ionic cationic exchange resins having salified acid groups, those preferred for the process of the present invention are those which have a polystyrene or sulphonated polyphenol or carboxylated polyphenol (polyacrylic) base, absolute preference being given to those absorbents of which the matrix consists of the product of copolymerization of styrene beads with a divinyl monomer such as divinylbenzene.

According to the process of the present invention, the halo-aldehyde is brought into contact first with an adsorbent solid having basic characteristics and then with adsorbent solid carrying salified acid groups, the said absorbents being chosen from the classes and products which have been previously defined. More particularly, in both stages of the process, the absorbent solid is brought into contact with the halo-aldehyde in liquid form.

Although in this treatment it is possible to operate at any temperature ranging from the melting temperature to the boiling temperature of the halo-aldehyde which is being subjected to purification, as a rule the lowest possible temperatures are maintained, in other words temperatures close to the melting point of the halo-aldehyde.

In practice, the temperatures used in the first stage of treatment range from ambient temperature (approximate 20° C) up to approximately 100° C.

In the choice of the temperature, within the aforesaid ranges, the nature of the adsorbent solid used for treatment is also taken into account. Thus, in the case of weak anionic resins, the working temperatures will in practice range from ambient temperature up to approximately 80° to 90° C, while in the case of strong anionic resins it will be appropriate not to exceed temperatures of approximately 50° C.

In the second stage of treatment, the temperatures used in practice will range from ambient temperature (20° C) up to approximately 130° C,.

It is not appropriate to exceed temperatures of 130° C since there is normally a lessening in the absorption capacity of the absorbent material.

The pressure used in the two stages of the purification process according to the present invention is not critical; normally, it is preferred to work at atmospheric pressure, but is is also possible to work at pressures above or below ambient pressures.

As has been stated previously, a basic aspect of the process according to the present invention is to work in the presence of water or alcohols in free form in that stage of purification in which the halo-aldehydes are brought into contact with an absorbent solid of basic characteristics. It has been found that the best conditions are achieved by, in this stage, maintaining a quantity of alcohol (generally methanol or ethanol) or water, in a free state, at the rate of 0.15 to 5.0% by weight with respect to the halo-aldehyde which is being purified, preferred values being around 0.5% by weight.

It is not suitable to go below 0.15% in that this will produce phenomena of polymerization of the aldehyde which is being subjected to polymerization.

The maximum quantity of free water or alcohol in the first stage of purification is not critical, but generally it is not suitable to rise above 5%, still calculated with respect to the halo-aldehyde which is being purified, in order not to render excessively burdensome the subsequent stage of purification.

We note in fact that in the subsequent treatment by absorbent solids carrying salified acid groups, elinination of the water or alcohols discharged jointly with the halo-aldehydes from the first stage of purification is achieved, inter alia. The addition of the water or alcohols may be performed in various ways. For example, the said substances may be added to the halo-aldehyde which is being subjected to purification or directly to the absorbent solid which is being used for the purpose. In the case of the water, the pre-treatment performed on the absorbent solid may be regulated in such a way that, at the end of the treatment, it has the desired level of water content. Therefore, any manner of addition is useful so long as a water or alcohol content of the level previously mentioned can be assured in the system. In the purification of halo-aldehydes according to the process of the present invention, any known technique may be employed in order to establish contact between liquid products and solid products. Thus, for example, it is possible in the first stage of purification to mix the halo-aldehyyde with the absorbent solid having basic characteristics, the solid products then being separated from the liquids. These latter are then, in the second stage of purification, mixed with the absorbent solid which carries the acid groups in the form of salts. However, in the preferred embodiment, the halo-aldehydes are supplied continuously to the end of a reactor which is of elongated form and which contains the absorbent solid of basic characteristics, the latter being in the form of a fixed bed.

Thus treated, the halo-aldehyde is then supplied continuously to the end of a second reactor containing the absorbent solid which carries the salified acid groups, again in the form of a fixed bed.

The purified halo-aldehyde is recovered at the other end of the second reactor.

According to another form of embodiment of the present invention, a single reactor is used which contains in succession a fixed bed of particles of absorbent solid having basic characteristics and a fixed bed of particles of absorbent solid carrying the salified acid groups. In the continuous performance of the process of the present invention, contact times relating to halo-aldehyde and solid absorbent are normally used which range from 5 to 10 minutes to 6 hours in the first purification stage, while in the second stage these times are maintained at 5 to 10 minutes to 1 hour.

The capacities of the absorbent solids of the present invention, in other words the quantity of purified product which can be obtained per unit of weight of absorbent solids, normally depends upon the quantity of impurities contained in the halo-aldehyde which is subjected to purification.

In any case, such absorbents may be regenerated by deabsorption of the impurities, according to normal methods known in the art, in other words the exhausted absorbent solids may be washed with a volatile solvent which is inert with respect to the monomer being purified, the said solvent preferably having a boiling point which is rather different from the boiling point of the monomer, in order to encourage its separation by distillation. Furthermore, it is preferable for the solvent to be soluble with water or alcohols insofar as regeneration of the absorbent requires treatment with an aqueous or alcoholic solution of alkaline hydroxides.

The solvents normally used for the purpose are generally alcohols, ethers or esters.

Regeneration of the absorbent may also be carried out at above the purification temperature and below the decomposition temperature of the absorbent, by treatment with nitrogen or another inert gas.

By proceeding according to the present invention, it is possible easily and conveniently to eliminate the impurities contained in the halo-aldehydes without giving rise to secondary reactions, such as for example polymerization or other undesirable side effects.

Therefore, the yield of purified halo-aldehydes is also very high.

The monomers which are purified in this way may be used in the preparation of polymers of high molecular weight, with high rates of polymerization and a low rate of consumption of polymerization catalyst.

Such desirable results which can be obtained in the process of polymerization are related to the purity of the halo-aldehydes obtained by the process according to the present invention.

In fact, as will become obvious from the following experimental examples, the said purified aldehydes have a halo-hydric acid content below 10 to 20 ppm and a water content below 20 ppm, while they are virtually free of other impurities.

EXAMPLE 1 (comparison)

A sample of 3000 g of pure commercial chloral having the following composition, as percentages by weight:

| | |
|---|---|
| hydrochloric acid | 0.085% |
| water | 0.5% |
| mono and dichloroacetaldehyde | 0.9% |
| chloral | 98.5%, |

is percolated at ambient temperature through a column containing 5A molecular sieves. The sieves are located in a steel column 120 cm high, 2.5 cm in diameter and provided with a system for maintaining anhydrous conditions in the medium, by means of a flow of nitrogen. The absorbent has been previously rendered anhydrous by being heated to 350° C under a stream of nitrogen (approximately 150 liters/hour).

The chloral is percolated at ambient temperature and at a rate of 250 to 300 ml/hour.

After percolation, a product is obtained which has the following composition:

| | |
|---|---|
| hydrochloric acid | 0.040% |
| water | 0.045% |
| mono and dichloroacetaldehyde | 0.9% |
| chloral | 98.9% |

1,500 g of chloral thus treated are subjected to fractional distillation. The product is filled into the vessel (capacity 2 liters) of a distillation apparatus comprising a column 1 m high and 2.6 cm in diameter, fitted with a Todd model reflux head and a means of collecting the distilled fraction.

The column is filled with Fenske rings with an inside diameter of 6 mm and an outside diameter of 7 mm.

The entire system is maintained in an inert atmosphere by passing a stream of nitrogen over the collection vessel.

The following fractions of distillate were drawn off:

| Fractions | grams | reflux ratio | Distillation temperature |
|---|---|---|---|
| 1a | 22.4 | 10:1 | up to 95° C |
| 2a | 75.3 | 10:1 | 95 - 97.5° C |
| 3a | 1278 | 2:1 | 97.5° C |

The fraction 3*a* was subjected to analysis and the following results were obtained:

| | |
|---|---|
| hydrochloric acid | 0.021% |
| water | 0.018% |
| mono and dichloroacetaldehyde | none |
| chloral | 99.9% |

The third fraction obtained by distillation is used for polymerisation carried out as follows:

An apparatus is used which consists of a flask of 500 ml, with 4 necks, fitted with an agitator and also a thermometer, dripper and connector adapted to maintain a stream of nitrogen. Since polymerization requires strictly anhydrous conditions, the apparatus is accurately supplied with nitrogen.

200 g of anhydrous n-heptane free from olefins and 210 mg of a solution of 23.7% by weight of lithium-butyl in n-heptane are introduced into the flask. Subsequently, the system is cooled by a solid carbon-dioxide-acetone mixture in a Dewar flask.

When the temperature inside the flask reaches −78° C, the agitator is set in motion and 22 g of monomer are gradually added. Agitation is continued at the said temperature for 20 hours after which 30 ml of methanol are added and ambient temperature restored.

The polymer suspension is filtered and the product thoroughly washed with acetone. Drying is carried out in a vacuum oven at 35°–40° C.

Subsequently, the product of polymerization is subjected to a treatment in a suspension of dimethylformamide at 130° C for 30 minutes, with a weight ratio of polymer to solvent equal to 1:8.

The percentages of polymer remaining after this treatment constitutes the fraction of polymer of high molecular weight.

The results of the test are summarized in Table 1, which shows the value of conversion of chloral in polymerization and the quantity of polymer of high molecular weight (HMW) as a percentage by weight of polymer.

EXAMPLE 2 (comparison)

A sample of pure commercial chloral identical to that in Example 1 is caused to percolate through a column of macroporous anionic exchanger resin (commercially known as Amberlite IRA-93) in hydroxylated form. The exchanger resin is placed in a glass column with an inside diameter of 2.5 cm and the height of 1 m fitted with an outer jacket for thermostatic control by circulation of oil.

The height of the resin bed is 95 cm. The wet resin filling is raised to a temperature of 120° C while a stream of anhydrous nitrogen is passed through it from the bottom upwards at a rate of approximately 150 liters/hour. In this way, the resin is rendered virtually anhydrous insofar as the residule moisture content is equal to or less than 0.1%, determined by the Karl Fischer method.

By working under strictly anhydrous conditions, by passing a stream of nitrogen through the medium, the sample of chloral is caused to percolate through the column at ambient temperature.

Already during the phase of filling of the column, the formation of a gelatinous solid will be noticed towards the bottom, this becoming progressively increased until it stops the flow of liquid.

The test is then interrupted and the solid recovered proves to be soluble in acetone, so indicating that the material is a chloral polymer of low molecular weight.

EXAMPLE 3

A sample of commercial chloral identical to that used in Example 1 is percolated at ambient temperature through a column of macroporous anionic exchanger resin (commercially known as Amberlite IRA-93) in hydroxylated form.

The same apparatus and the same quantity of absorbent are used as in Example 2. The resin placed in the apparatus has a moisture content equal to approximately 1.5%.

By working under strictly inert conditions, by passing a stream of nitrogen through the medium, the chloral is percolated at the rate of 250 to 300 ml/hour. No visible phenomenon of polymerization is observed along the column and analysis of the percolated product shows the following results:

| | |
|---|---|
| hydrochloric acid | less than 0.002% |
| water | 0.154% |
| mono- and dichloroacetaldehyde | 0.9% |
| chloral | 99.3% |

After having percolated a quantity of chloral corresponding to 50 kg of chloral to every kg of resin, the values revealed by analysis of the percolated product are virtually identical to those listed above. 2000 g of chloral which have been thus treated are percolated at ambient temperature through a column of macroporous cationic exchanger resin (commercially known as Amberlite 200) having sulphonic groups salified with sodium. The resin is placed in a glass column identical to that of Example 2. The height of the bed is 95 cm. The wet resin placed in the apparatus is raised to a temperature of 160° C while a stream of anhydrous nitrogen is passed through it from the bottom upwards at a rate of 150–180 liters/hour. In this way, the resin is made virtually anhydrous in that the residual moisture content is equal to or less than 0.1% determined by the Karl Fischer method.

Working under strictly anhydrous conditions, by passing a stream of nitrogen over the top of the column, the sample of chloral is percolated at the rate of 250–300 ml/hour.

The resultant chloral was analyzed and the following results obtained:

| | |
|---|---|
| hydrochloric acid | 0.002% |
| water | 0.009% |
| mono- and dichloroacetaldehyde | 0.9% |
| chloral | 99.0% |

1500 g of the percolated chloral were finally subjected to distillation, using the apparatus described in the first example.

The following fractions of distillate were drawn off:

| Fractions | grams | reflux ratio | distillation temperature |
|---|---|---|---|
| 1 | 23.8 | 10:1 | up to 95.5° C |
| 2 | 1307 | 2:1 | 97.5° C. |

Analysis of fraction No. 2 shows the following results:

| | |
|---|---|
| hydrochloric acid | equal to or less than 20 ppm |
| water | equal to or less than 20 ppm. |
| mono and dichloroacetaldehyde | none |

Example No. 2 obtained by distillation is used for a polymerization test carried out in the manner described in the first example.

The polymer obtained is subjected to test with dimethylformamide to determine the fraction of high molecular weight. The results are summarized in Table 1.

Table 1

| Examples | Conversion rate | HMW |
|---|---|---|
| 1 | 25.4% | 53.3% |
| 3 | 78.3% | 92.6% |

EXAMPLE 4 (comparison)

Into a glass flask of 5 liters capacity and with four necks, fitted with an agitator and also a thermometer and bulb-type cooler, maintained under anhydrous conditions and by passing a stream of nitrogen over the top of the condenser are introduced 3500 g of pure commercial chloral and 300 g of finely ground pure calcium carbonate.

Composition of the chloral is as follows:

| | |
|---|---|
| hydrochloric acid | 0.75% |
| water | 0.25% |
| chloral | 98.9% |

After the agitator has been set in operation, the system is heated by immersion in a thermostatically controlled oil bath at a temperature of 80° C.

At intervals, analyses are carried out to determine the hydrochloric acid content and the results are summarized in Table 2.

Table 2

| Hours of treatment | % HCl |
|---|---|
| 0 | 0.75 |
| 5 | 0.34 |
| 12 | 0.16 |
| 20 | 0.044 |
| 24 | 0.041 |
| 26 | 0.040 |
| 30 | 0.040 |

After cooling, the chloral is filtered under nitrogen, by applying a slight over-pressure through a separating tube fitted with a porous filter, and introduced into another 5 liter flask.

While the system is maintained in an inert atmosphere by means of nitrogen, 200 g of calcium sulphate (previously dried for several hours in an oven at 300° C) are added.

The result is left to stand for 24 hours, being stirred from time to time, and at ambient temperature, and finally the chloral is filtered in the manner previously described.

Analysis revealed that the chloral has the following composition:

| | |
|---|---|
| hydrochloric acid | 0.04% |
| water | 0.025% |
| chloral | 99.9% |

The said chloral is subjected to polymerization in the manner previously described and using different quantities of catalyst.

Zinc butyl in a heptane solution is used as the catalyst. The results are shown in Table 3.

The said tables show three tests for example 4, in which polymerisation is carried out with a molar ratio (R) of catalyst to monomer equal to 0.5, 2.0 and 5.0 respectively. The table also shows the percentage conversion rate with respect to the monomer.

EXAMPLE 5

3.5 kg pure commercial chloral identical to that of Example 4, are placed in a 5-liter flask with three necks, containing 70 g of macroporous exchanger resin of the anionic type, in hydroxylated form (Amberlite IRA-93). The resin has been previously rendered anhydrous by being heated to 120° C in a stream of nitrogen. The residual moisture content after such treatment is equal to 0.095%, determined by the Karl Fischer method. The flask is fitted with an agitator and also a cooling apparatus. Anhydrous conditions obtained by virtue of a stream of nitrogen washing over the top. It is left at ambient temperature and under agitation for 3 hours. It is then left to decant and the liquid is siphoned off through a tube introducing into the flask, by application of a slight over-pressure.

The result is a chloral to the following composition:

| | |
|---|---|
| hydrochloric acid | equal to or less than 0.002% |
| water | 0.120% |
| chloral | 99.85% |

The chloral is then percolated through a column of macroporous cationic exchanger resin (commercially known as Amberlyst-15) having the sulphonic groups salified with calcium. The column of resin is made up in exactly the same way as with Example 3.

Percolation of the chloral takes place at ambient temperature and in a manner identical to that described in Example 3.

After treatment, the chloral has the following composition:

| | |
|---|---|
| hydrochloric acid | equal to or less than 0.002% |
| water | equal to or less than 0.002% |
| chloral | 99.9% |

Tests are then carried out on the purified chloral with respect to polymerization, using zinc butyl as a catalyst. Table 3 shows the results.

Table 3

| Example | Test | R | Conversion % |
|---|---|---|---|
| 4 | 1 | 0.5 | 1 |
| 4 | 2 | 2.0 | 5.8 |
| 4 | 3 | 5.0 | 42.3 |
| 5 | 1 | 0.25 | 32.5 |
| 5 | 2 | 0.50 | 78.4 |

EXAMPLE 6

3000 g of dichloroacetaldehyde containing:

| | |
|---|---|
| hydrochloric acid | 0.80% |
| water | 0.05% |
| ethanol | 0.15% |

are percolated through a column of macroporous anionic resin in anhydrous hydroxylated form (Amberlite IRA-904), to which ethanol has been added. The same apparatus and procedures are used as in Example 2, a percolation rate equal to 300–350 ml/hour being maintained. Analysis of the percolated product yielded the following results:

| | |
|---|---|
| hydrochloric acid | 23 ppm |
| water | 35 ppm |
| ethanol | 980 ppm |

The product thus treated is subsequently percolated through a column of macroporous cationic resin, the sulphonic groups of which are salified with potassium (Amberlite A-200). The resin is already anhydrous, having had nitrogen passed over it at 160° C. Percolation is carried out at ambient temperature, using the method previously described.

Analysis of the percolated product provided the following results:

| | |
|---|---|
| hydrochloric acid | equal to or less than 20 ppm |
| water | equal to or less than 20 ppm |
| ethanol | equal to or less than 20 ppm. |

What we claim is:

1. A process for the purification of halo-aldehydes selected from the group consisting of monochloroacetaldehyde, dichloroacetaldehyde, trichloroacetaldehyde, monofluoroacetaldehyde, difluoroacetaldehyde, trifluoroacetaldehyde, bromoacetaldehyde and alpha-alpha-beta-trichloro-n-butyraldehyde, wherein in conducting a first stage of purification the said halo-aldehydes, in liquid form, are brought into contact with an absorbent solid consisting of an anionic exchange resin consisting of a polystyrene exchange resin having quaternary ammonium groups bonded thereto, said first stage being carried out in the presence of a free alcohol selected from the group consisting of methanol and ethanol or water in quantities of 0.15 to 5.0% by weight with respect to the halo-aldehydes, and conducting a second stage of purification wherein said halo-aldehyde, thus treated and in liquid form, is brought into contact with an absorbent solid consisting of a cationic exchange resin consisting of a polystyrene exchange resin having sulfonic groups linked thereto and in the form of salts of alkali or alkaline earth metals, said process being carried out at a temperature from the melting temperature to the boiling temperature of said halo-aldehyde.

2. A process according to claim 1, wherein in said first stage of purification, purification is performed with a quantity of free alcohols or water around 0.5% by weight with respect to the halo-aldehyde.

3. A process according to claim 1, wherein said free alcohol is methanol or ethanol.

4. A process according to claim 1, wherein said absorbent solid used in said first stage of purification consists of an anionic exchange resin, the matrix of which is composed of the product of copolymerization of styrene beads with a divinyl monomer such as divinylbenzene.

5. A process according to claim 1, wherein said absorbent solid used in said first stage of purification has a specific surface area equal to at least 0.5 sq.m/g and contains pores with a diameter ranging from 20 to $2 \times 10^4$ Angstrom units.

6. A process according to claim 5, wherein said specific surface area is equal to at least 10 sq.m/g.

7. A process according to claim 1, wherein said absorbent solid used in said second stage of purification consists of salts of alkali or alkaline earth metals with cationic exchange resins, the matrix of which consists of the products of copolymerization of styrene beads with divinylbenzene.

8. A process according to claim 1, wherein said absorbent solid used in said second stage of purification has a specific surface equal to 1 sq.m/g and contains pores with a diameter ranging from $10^{1.3}$ to $10^5$ Angstrom units.

9. A process according to claim 1, wherein said second stage of purification is carried out at temperatures ranging from ambient temperature up to approximately 130° C.

10. A process according to claim 4, wherein the divinyl monomer is divinylbenzene.

11. A process according to claim 1, wherein the product of said second stage of purification consists essentially of purified aldehydes having a halohydric acid content below 10 to 20 ppm and a water content below 20 ppm, being virtually free of other impurities.

12. A process according to claim 1, wherein a single halo-aldehyde is purified.

13. A process according to claim 1, wherein said halo-aldehydes contain halohydric acid as an impurity, said halohydric acid being substantially completely removed in said first stage purification, and said free water or alcohol are substantially completely removed in said second stage purification.

* * * * *